United States Patent [19]

Ranford

[11] Patent Number: 4,798,578

[45] Date of Patent: Jan. 17, 1989

[54] AUTOTRANSFUSION DEVICE

[75] Inventor: Alan B. Ranford, St. Louis, Mo.

[73] Assignee: Sherwood Medical Company, St. Louis, Mo.

[21] Appl. No.: 14,508

[22] Filed: Feb. 13, 1987

[51] Int. Cl.$^4$ .............................................. A61M 1/03
[52] U.S. Cl. ........................................ 604/4; 604/319; 604/408
[58] Field of Search ........................... 604/4-6, 604/319-321, 252, 408-410

[56] References Cited

U.S. PATENT DOCUMENTS

| | | | |
|---|---|---|---|
| 3,473,532 | 10/1969 | Eisenberg | 128/227 |
| 3,557,786 | 1/1971 | Barr et al. | 604/252 |
| 3,734,154 | 5/1973 | Polk | 150/9 |
| 4,006,745 | 2/1977 | Sorenson et al. | 604/4 |
| 4,105,031 | 8/1978 | Kurtz et al. | 128/276 |
| 4,161,179 | 7/1979 | Abramson | 128/278 |
| 4,429,693 | 2/1984 | Blake et al. | 604/73 |
| 4,443,220 | 4/1984 | Hauer et al. | 604/4 |
| 4,540,413 | 9/1985 | Russo | 604/320 |
| 4,583,972 | 4/1986 | Hunter, III et al. | 604/133 |

FOREIGN PATENT DOCUMENTS 2330101 1/1975 Fed. Rep. of Germany .
1049763 12/1953 France .

OTHER PUBLICATIONS

Deknatel, "Why transfuse if you can reinfuse with the Pleur-Evao ® Autotransfusion System?", The Journal of Thoracic and Cardiovascular Surgery, vol. 93, No. 2, Feb. 1987.

Primary Examiner—Dalton L. Truluck
Attorney, Agent, or Firm—Stanley N. Garber; Andrew J. Beck; William R. O'3 Meara

[57] ABSTRACT

An autotransfusion device for use with a chest drainage unit is disclosed which includes a collapsible blood collection bag assembly having slotted stiffener members and a holder for holding the stiffener members bowed outwardly and the bag expanded for collecting blood. The bag assembly is removable from the holder for infusing the collected blood into the patient. An inlet and a gas outlet are at the top of the bag, and a filter is arranged to filter blood from the inlet to a blood collection portion of the bag, but air from the inlet can flow to the gas outlet without flowing through the filter.

18 Claims, 4 Drawing Sheets

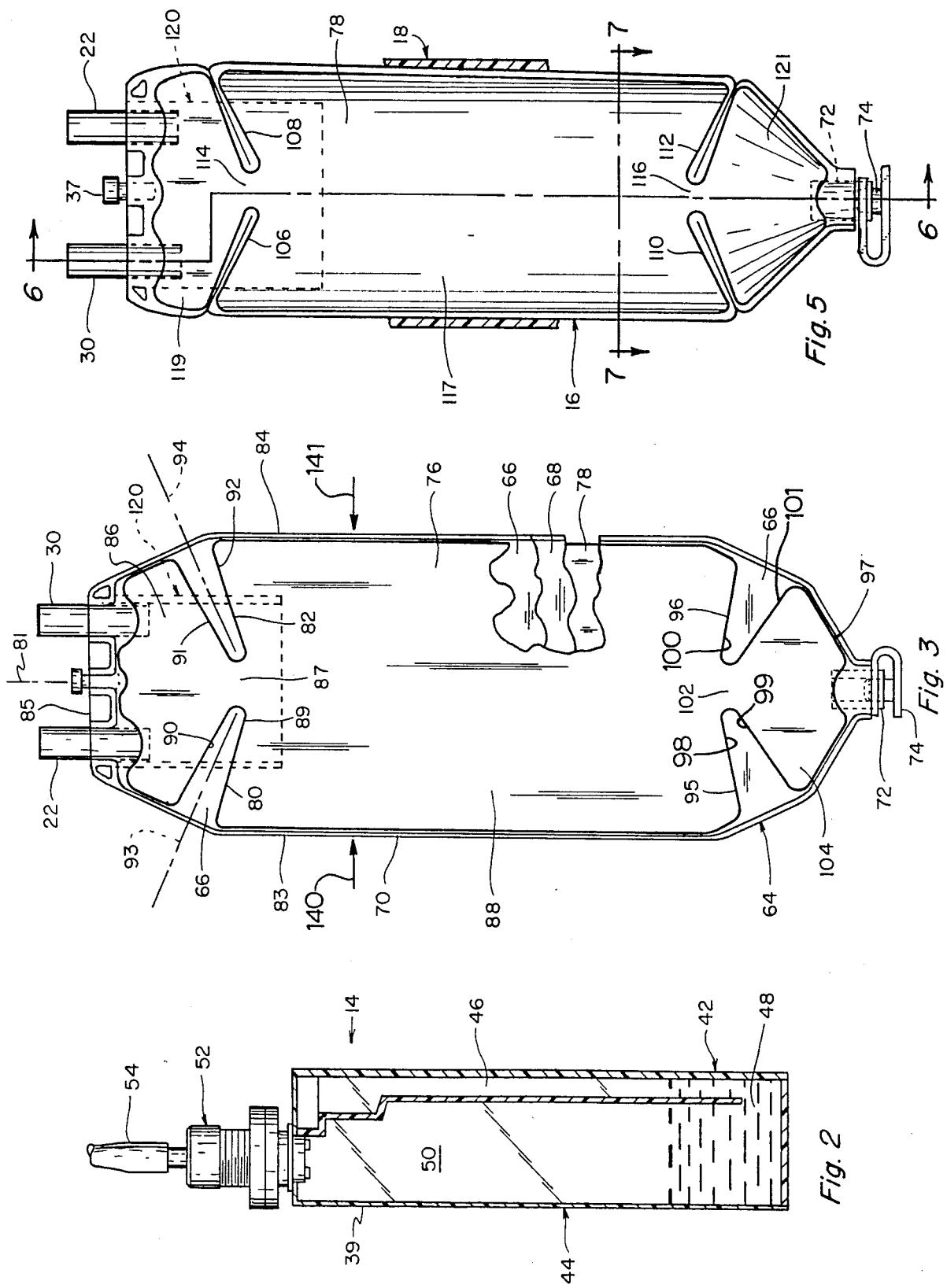

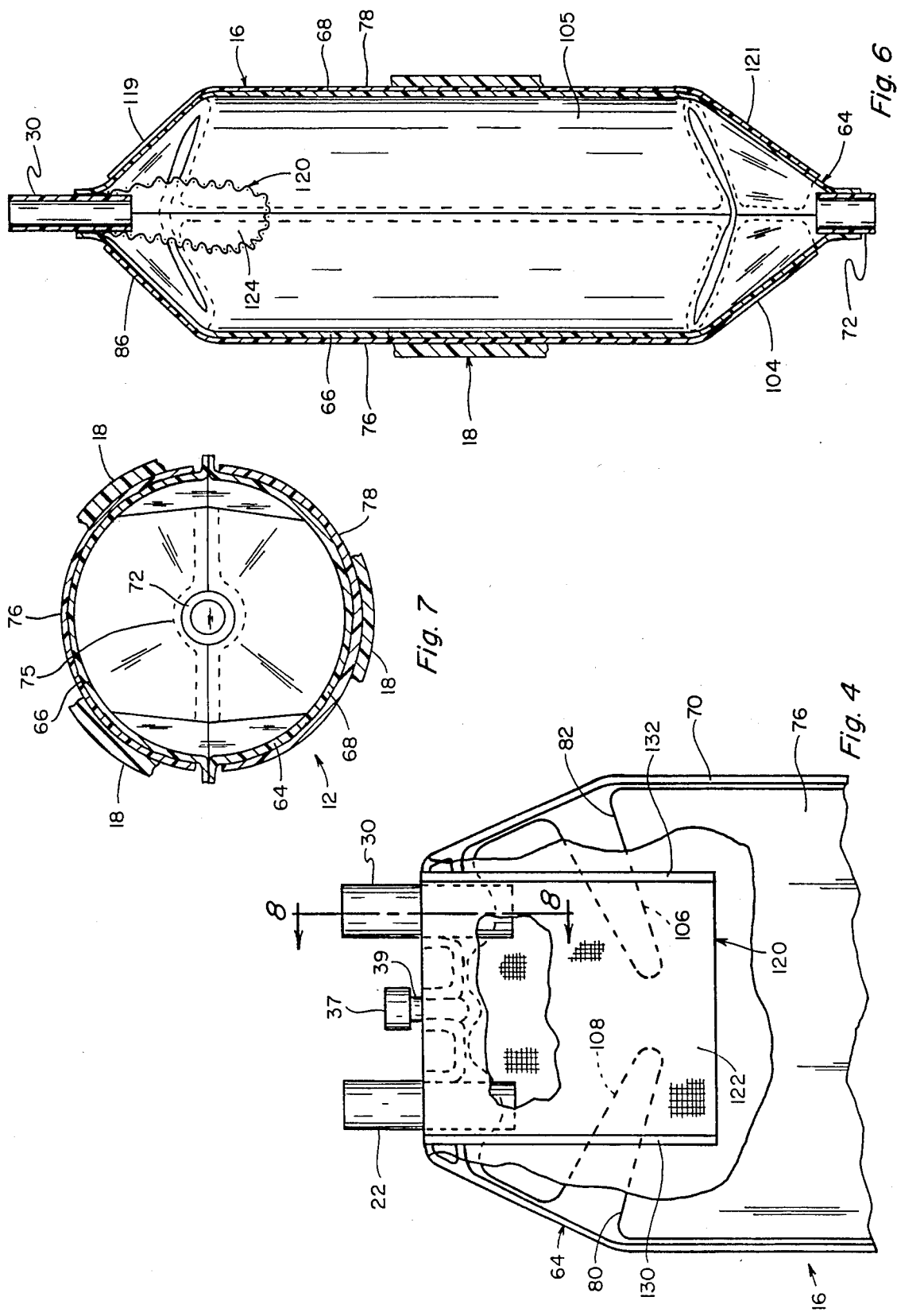

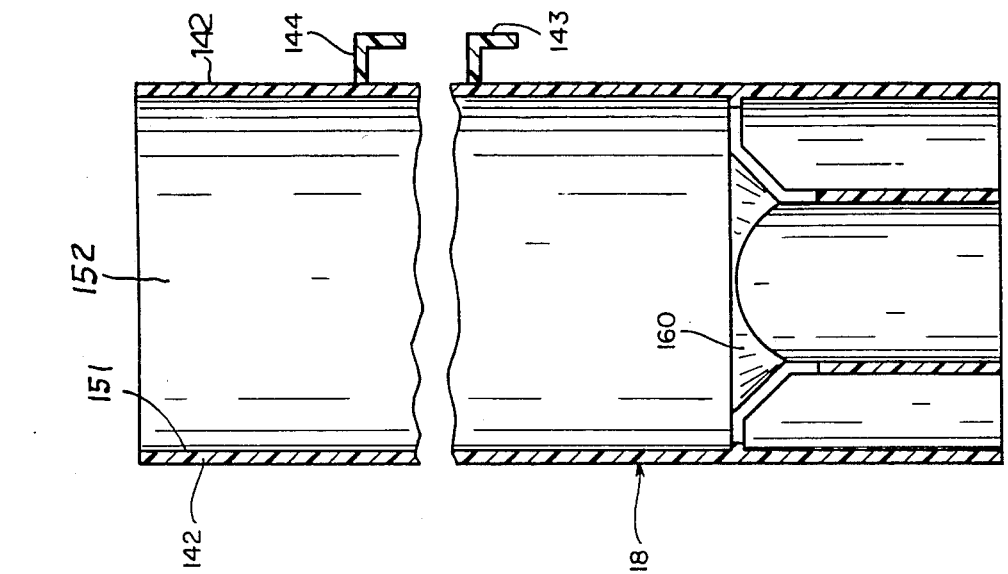
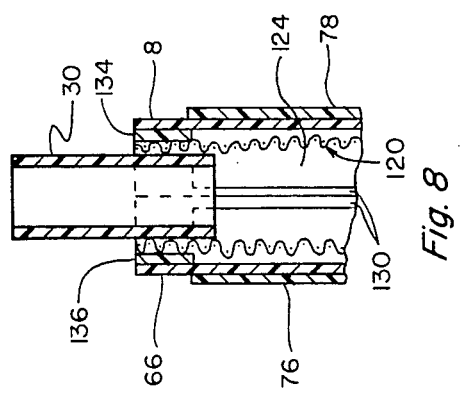
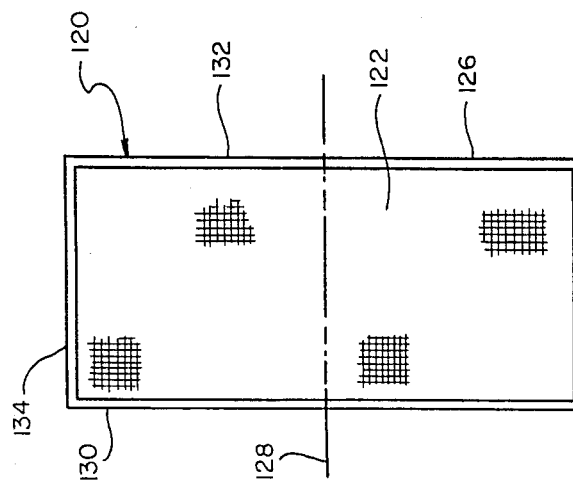
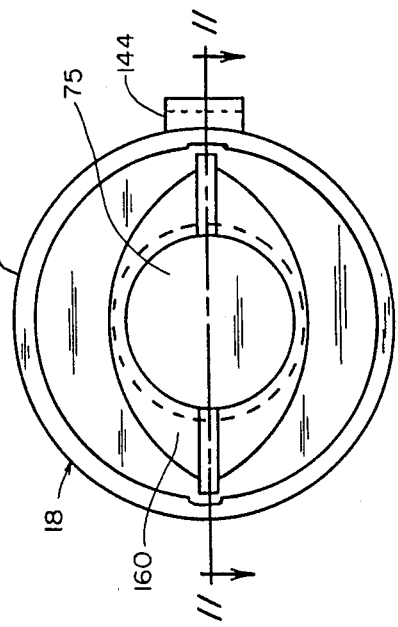

AUTOTRANSFUSION DEVICE

TECHNICAL FIELD

This invention relates to autotransfusion devices and more particularly to autotransfusion devices subjected to negative pressures during blood collection.

BACKGROUND

More recently, auxiliary autotransfusion blood collection containers have been employed with chest drainage units which permit reinfusion of the collected blood to the patient thereby avoiding the necessity of infusing stored blood from another person and the possibility of transmitting a disease to the patient.

Some autotransfusion devices of this type have had certain problems or disadvantages associated with them. A blood collection bottle which is non-collapsible has been connected to a chest drainage unit such that suction is applied through the bottle to the plueral cavity of a patient with the bottle receiving drainage blood. In order to reinfuse the blood into the patient, the bottle must be vented to atmosphere to allow the collected blood to flow from the bottle to the patient. In such a case, air is in contact with the blood and may effect its characteristics. Also, an air filter should be used to filter air from the atmosphere into the container during infusion.

Collapsible bag blood collection containers have also been used in order to avoid the necessity and problems of venting the container during reinfusion. However, such collapsible bag-type containers have also had certain problems and disadvantages. For example, the collapsible bag requires apparatus to maintain the bag in an expanded condition during blood collection in spite of the negative pressures or suction forces within the bag. This has caused, in some cases, the bag and the bag expanding device to be complicated and expensive, and in general, such bags when expanded may take on indefinite shapes and produce indefinite volumes and produce inaccurate indications of the amount of blood collected at any time.

Because drainage fluids from the plueral cavity contain solids or semisolids, known autotransufusion devices employ a filter placed in the patient drain line. This placement of the inlet filter creates several problems in use. In most cases during the initial stages of recovery from pneumo-thoracic surgery there is some leakgage of air at the wound site. The air passes with the blood, through the filter thus producing bubbling and foaming of blood. Such foaming gradually fills the air space in the device making it more difficult to determine the amount of blood collected at any given time and also creating a problem by expelling blood as well as air when the collection bag is squeezed to expell air prior to reinfusion of the patient's blood.

OBJECTS AND SUMMARY OF THE INVENTION

It is therefore an object of the present invention to provide an improved blood collection and reinfusion device which is collapsible and which can be maintained in a predetermined expanded condition during blood collection and wherein the above-mentioned problems are substantially obviated. Another object is to provide an improved autotransfusion blood collection device which is expandable for collecting blood with suction applied thereto while maintaining a predetermined expanded condition and which is collapsible for reinfusion purposes. Still another object is to provide an improved autotransfusion device adapted for connection with a chest drainage unit which substantially avoids the above-mentioned disadvantages associated with collapsible bag autotransfusion devices.

In accordance with one aspect of the present invention, an autotransfusion device is provided with includes a collapsible blood collection bag, and a pair of stiffening members connected to the opposed sides of the bag which are flexible in response to forces tending to move the opposed sides thereof toward each other to expand the bag for collecting blood. Each end of each of the stiffener members is provided with a pair of slots extending from the opposed sides of the member inwardly at an angle to the longitudinal axis of the bag, the slots allowing the bag to form inclined surfaces at each of the opposite ends thereof when the bag is expanded for collecting blood.

In accordance with another aspect of the present invention, an autotransfusion blood collection and reinfusion device is provided which includes a blood collection chamber having an inlet for connection to a patient and a gas outlet for connection with a source of negative pressure during blood collection. A filter in the chamber is connected to filter blood flowing from the inlet to a blood collection portion of the chamber but gas can flow from the inlet to the gas outlet without flowing through the filter.

In accordance with still another aspect of the present invention, an autotransfusion device is provided which includes a collapsible bag and stiffens for expanding the bag when forces are maintained on the stiffeners tending to move the opposed side edges toward each other, and a holder for receiving the bag and the stiffener members to maintain the bag in an expanded condition for receiving blood. The holder is generally cylindrical and has means for releasably connecting it to a chest drainage unit.

These as well as other objects and advantages of the present invention will become apparent from the following detailed description and accompanying drawings.

BRIEF DESCRIPTION OF THE DRAWINGS

FIG. 2 is a cross-sectional view taken along the line 2—2 of FIG. 1;

FIG. 3 is an enlarged side view of the bag assembly of FIG. 1 but in its unrestrained or free state condition;

FIG. 4 is an enlarged partial side view of the upper portion of the bag assembly of FIG. 3 with parts broken away;

FIG. 5 is an enlarged side elevational view of the autotransfusion device of FIG. 1 rotated 180° about the vertical axis with the holder of FIG. 1 broken away and parts removed;

FIG. 6 is a cross-sectional view taken along the line 6—6 of FIG. 5;

FIG. 7 is a cross-sectional view taken along the line 7—7 of FIG. 5;

FIG. 8 is a cross-sectional view taken along the line 8—8 of FIG. 4.

FIG. 9 is a plan view of the filter of FIG. 1 during a stange in the manufacture of the device of FIG. 1;

FIG. 10 is a top view of the holder of FIG. 1 when apart from the other apparatus of FIG. 1; and FIG. 11 is a cross-sectional elevational view of the holder of FIG. 10.

DESCRIPTION OF THE PREFERRED EMBODIMENT

Figure 1:
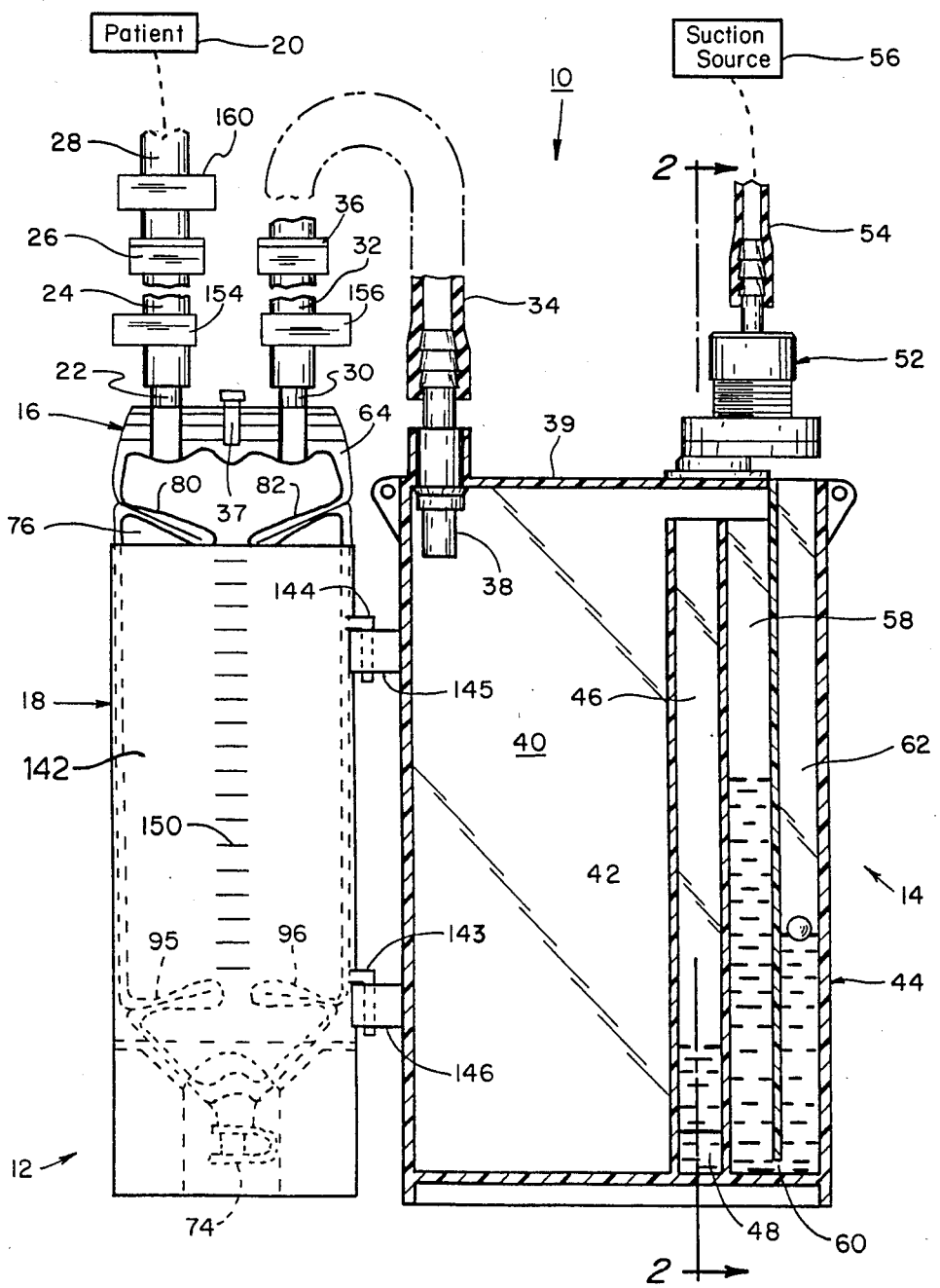
FIG. 1 is an elevational view, partly in section, of a chest drainage system including an autotransfusion device in accordance with a preferred embodiment of the present invention.

Referring now to the drawings and particularly FIG. 1, a chest drainage system 10 is shown including an autotransfusion blood collection device 12 connected to the side of a chest drainage unit 14. The device 12 includes an autotransfusion or blood collection or reinfusion bag assembly 16 and a bag expanding member or holder 18 receiving the bag assembly 18. Holder 18 is releasably connected to the side of the chest drainage unit 14. As will be discussed hereafter, the holder 18 maintains the collapsible bag assembly 16 in an expanded condition for receiving body fluids from the plueral cavity of a patient indicated at 20.

The collapsible blood collection and reinfusion bag assembly 16 has an inlet 22 communicating with the interior of the bag assembly and shown connected to a tube 24. Tube 24 is connected through a tube connector 26 to the proximal end of a patient tube 28 which is connected through a catheter to the plueral cavity of patient 20. Spaced from the inlet 22 at the top of the bag assembly 16 is a gas outlet 30 communicating with the interior of the bag assembly and inlet 22. Gas outlet 30 is connected to a tube 32 which, in turn, is connected to a tube 34 through a tube connector 36. Tube 34 is connected to an inlet 38 of the cheest drainage unit 14. An auxiliary inlet 37 between the inlet and outlets 22 and 30 communicates with the interior of the bag and is preferably a self-sealing seal which can be penetrated by a syringe needle for introducing a substance to the bag assembly 16, for example, an anticoagulant.

Chest drainage unit 14 is shown for illustration including a housing 39, preferably of rigid transparent plastic, for example, a polycarbonate or the like. The housing 39 includes a fluid collection chamber 40, an underwater seal chamber indicated generally at 42, and a liquid manometer indicated at 44. The liquid underwater seal includes a relatively narrow vertical channel 46 open at the top where it is in fluid communication with a collection chamber 40. Channel 46 has an opening 48 at the bottom which communicates with a relatively large gas chamber 50 of the water seal 42 as seen in FIG. 2. Connected to the top of outlet chamber 50 is a suction regulator 52 that is connected by a flexible tube 54 to a source of suction 56 (FIG. 1) which sources may be a conventional hospital wall suction source. The liquid manometer includes a vertical channel 58 connected in fluid communication with collection chamber 40 at the top and by a passage 60 at the bottom to a vertical column 62 that is open at the top to atmosphere. Both the underwater seal 42 and the liquid manometer 44 are shown provided with suitable quantities of a liquid such as water.

When the chest drainage system 10 is operating, a partial vacuum or negative pressure exists in the underwater seal chamber 50 (FIG. 2), and any air or gas from the patient flows from tube 28 into the upper portion of bag assembly 16 through inlet 22, then, into outlet 30, into collection chamber 40, downwardly through the water in underwater seal channel 46, through the bottom opening 48, upwardly through the water in outlet chamber 50 (FIG. 2) and then to the suction source 56. The underwater seal 42 prevents any atmospheric air from flowing through the unit to the patient. Because the liquid manometer is responsive to the pressure in collection chamber 40, the level of the liquid in the liquid manometer 44 will vary in height in accordance with negative pressure changes in the collection chamber, thus providing an indication of the suction level or negative pressure in the collection chamber and therefore in the plueral cavity of the patient. The regulator 52 regulates and limits the suction or negative pressure in the collection chamber 40 to a desired and safe value. The construction and operation of the chest drainage unit 14 including that of the suction regulator 52 are shown described in detail in U.S. Pat. No. 4,372,336 and are hereby incorporated herein by reference.

The collapsible blood collection and reinfusion bag assembly 16 is shown in FIGS. 3 and 4 in its unrestrained or free condition, that is, without any compressive forces being applied to the assembly so that the assembly is in its substantially flat condition prior to being inserted into the holder 18. Assembly 16 includes a collapsible pliable blood collection and reinfusion bag 64 formed of a pair of opposed sheet members or panels 66 and 68 sealed together about the periphery of the bag such as indicated by a peripheral seam 70 and which may be a heat seal. The pheripheral seal 70 extends around the tubular inlet 22 and a gas outlet 30 to seal them at the top of the bag assembly in communication with the interior of the bag. Also, the seal 70 extends around seals a tubular blood outlet 72 at the bottom of the assembly. The blood outlet 72 is closable by a plug 74 integrally tethered to the bag 64. The blood outlet 72 is shown in FIG. 7 provided with a conventional pierca-ble seal 75. Plug 74 maintains the seal 75 clean. The panels 66 and 68 of bag assembly 16 are preferably formed of pliable material such as a relatively soft polyvinyl chloride so that the bag is readily and easily collapsible.

Bag assembly 16 also includes a pair of flexible bag stiffener members 76 and 78 respectively fixed to the outer surfaces of front and back panels 66 and 68 of bag 64. Stiffener members of panels 76 and 78 are in the form of generally flat sheet members of relatively stiff material, preferably, of a relatively rigid, resilient plastic sheet material such as polyester terephthaltate (PET-G) sheet material.

Preferably, the stiffening members 76 and 78 are identical in shape to each other in the illustrated embodiment, and only panel 76 is shown in its flattened condition as in FIG. 3. Also, in the illustrated embodiment, each of the stiffener panels 76 and 78 is symmetrical about the vertical or longitudinal axis 81 in FIG. 3. Panel 76 is provided with a pair of slots 80 and 82 which extend inwardly respectively from the opposed sides of the panel, indicated at 83 and 84, are are near, but spaced from, the upper edge 85 of the panel so that an upper portion 86 above the slots has a relatively narrow neck 87 integrally connecting the upper portion 86 to a relatively large main portion 88. The slots 80 and 82 intersect the periphery of the stiffener member and have opposed pairs of opposed sidewalls 89 and 90, and 91 and 92, respectively, the slots narrowing toward the inner ends. The longitudinal axes of the slots, indicated at 93 and 94 in FIG. 3, cross approximately at the longitudinal axis 81 with the slot axes being at an angle of about 22° with respect to a lateral or horizontal line intersecting the axes. Panel 76 also has a pair of slots 95 and 96 adjacent to but spaced from the bottom edge indicated at 97, and which extend respectively from the sidewalls 83 and 84 inwardly. Slots 95 and 96 also are widest at the periphery and have opposed sidewalls 98 and 99, and 100 and 101. The slots 95 and 96 also have axes which intersect the vertical axis 80 and are at about 22° to a horizontal line. The inner ends of the slots 95 and 96 are spaced from each other to provide a relatively narrow neck portion 102 that connects a lower portion 104 to the major central portion 88. The neck portions 87 and 102 between the inner ends of the two pairs of slots are relatively narrow so that they are relatively flexible and readily bend to allow the upper, main and lower portions of each stiffener member to curve in different planes to form the expanded bag assembly 16 when when opposed compressive forces are applied to the opposed sides 83 and 84 of the assembly which applies the forces to the opposed side edges of the stiffener members 76 and 78. The bag assembly 16 thus has an essentially cylindrical central portion, and inclined upper and lower portions when inserted into the holder 18, as seen in FIGS. 5, 6, 7.

The back stiffener member 78 is identical to stiffener member 76 as described above. The stiffener member 78, is best seen in FIG. 5 and 6 where the bag assembly 16 is shown in its expanded condition in the holder 18. Member 78 has an upper pair of slots 106 and 108 (identical to slots 80 and 82 in stiffener member 76) and a lower pair of slots 110 and 112 (identical to slots 95 and 96 in stiffener member 76). Stiffener member 78 also has upper and lower narrow neck portions 114 and 116 between the inner portions 114 and 116 between the inner ends of the pairs of slots which connect the main portion 117 with upper and lower stiffener end portions 119 and 121 respectively. The two stiffener members 76 and 78 are fixed to the bag 64 with the corresponding slots and portions of the two stiffener members in registration.

Connected within the upper portions of bag 64 is a filter 120, as best seen in FIGS. 4, 6, 8 and 9. The illustrated filter 120 is shown including a fine plastic screen 122 in the form of a filter bag having a filter chamber 124 closed about its periphery with the inlet 22 and gas outlet 30 sealed to the filter and extending from the exterior of bag assembly 16 into the filter chamber 124.

Filter 120 may be formed by cutting suitable filtering screen material 122 into rectangular shape as shown in FIG. 9. Then a plastic frame formed from sheet material, such as a thermoplastic, for example, a polyvinyl chloride can be melt bonded to the periphery to form a border indicated at 126. Then the thus formed element can be folded in half, such as along the fold line 128, and the opposed sides 128 and 130 fused or melt bonded together and with the opposed ends 134 and 136 heat sealed together and about the inlet 22, outlet 30, and auxiliary inlet 37.

After the collection bag panels 66 and 68 have the stiffener members 76 and 78 secured thereto the peripheral seal 70 is formed in order to seal the peripheries of panels 66 and 68 together and with the upper portion of the filter 120, including the ends 134 and 136 (FIG. 9), sealed to and between the panels 66 and 78 at the top end 85 of the bag assembly 16. The upper end of the filter 120 is preferably sandwiched between the panels 66 and 68 at the top and heat welded or otherwise sealed between the panels 66 and 68. FIG. 10 shows a top view of the bag assembly 16 as viewed in FIG. 3.

When opposed compressive forces are applied to the opposed lateral sides 83 and 84 of the bag assembly 16 (FIG. 3), that is, forces in the direction of arrows 140 and 141, the central portions of stiffener members 76 and 78 bow outwardly in opposite directions from each other. That is, the main central portions of stiffener members 76 and 78 bow in opposite directions from each other tending to take a generally circular cross-section and carry the wall of the bag with them outwardly. When such forces are applied, and the assembly 16 is inserted into the tubular holder 18, the bag is expanded as indicated in FIGS. 1, 5, 6 and 7. As the opposed side edges 80 and 84 of assembly 16, including the adjacent side edges of the stiffener members 76 and 78, are moved toward each other in response to such compressive forces, the sidewalls or edges of each of the slots 80, 82, 95, 96, 106, 108, 110 and 112 move toward each other tending to close the slot as seen in FIGS. 1 and 5.

The slots being wider at the mouth near the periphery of the bag assembly 16 permit the slots to close and allow the bag to readily assume the wedge shape at the top of the assembly and generally conical shape at the bottom of the assembly. The relatively narrow neck portions 87 and 102 of stiffener member 76 and neck portions 114 and 116 of panel 78 readily bend to allow the upper and lower portions of the assemby 16 to readily become inclined when the bag is expanded into a generally cylindrical shape. The stiffener members 76 and 78 are preferably connected substantially over their entire surfaces to the bag panels 66 and 68 respectively to cause the bag panels to bow outwardly with the stiffener members. Preferably, the stiffener members and bag panels are heat bonded or welded together over the entire meeting surfaces. However, a suitable adhesive could be used in some cases.

With this construction, the bag assembly 16 readily takes on the desired predetermined configuration and which will be maintained at the normal levels of suction used so that each bag manufactured will have substantially the same predetermined internal volume during operation of the chest drainage system and such assemblies can therefore be calibrated to provide relatively acurate indications of the volume of blood collected at any time. Calibration are shown at 150 on the holder 18 in FIG. 1 and may include graduations in centiliters.

The holder 18, as shown also in FIGS. 10 and 11, includes a substantially rigid cylindrical member or housing 142 having suitable lugs 143 and 144 integrally connected thereto for supporting engagement with suitable receptors 145 and 146 mounted onto one side of the chest drainage unit 14 as shown in FIG. 1. Where desired, a releasable spring latch (not shown) may be provided on the holder 18 such as between the lugs and a cooperating latch pin (not shown) on the side of chest drainage unit 14. Such a latch and pin would ensure that the autotransfusion device 12 and unit 14 would remain together during use and facilitate easy removal of the autotransfusion unit from the chest drainage unit and replacement.

The holder 18 has a cylindrical inner wall 151 providing a cylindrical chamber 152 for receiving and maintaining the bag assembly 16 in a generally cylindrical shape. That is, the opposed sides of the chamber or diameter in the illustrated embodiment are sized relative to the width of the bag assembly 16 such that the chamber walls 151 continuously exert the necessary opposed compressive forces on the opposed side edges of the stiffener members adjacent the opposed sides 83 and 84 (FIG. 3). of the bag assembly 16 to maintain the bag assembly in an expanded condition as shown.

Near the bottom of the holder 18 is a generally elliptical and inclined surface indicated a 160 in FIGS. 10 and 11 which supports the generally conical bottom end of the bag assembly 16 to properly locate it within the holder, the bottom of the bag assembly being generally conical and somewhat elliptical at the bottom. The bottom of the assembly 16 rests on the surface 160.

In operation, when the chest drainage system 10 is connected as shown, blood and gas flow from the plueral cavity of patient 20 through the inlet 22 into the interior of filter 120. Blood filters through the filter and flows downwradly into the blood collection chamber 105 of the bag 64 while gas and air from the inlet 22 flows under the force of suction to the interior or filter bag and then, without passing the filter, into the gas outlet 30. The gas flows from outlet 30 into tube 34 and the chamber 40 by way of inlet 38 of the chest drainage unit 14. Filter 120 catches solid or semi-solid particles within the filter bag allowing filtered blood to flow into the main collection portion 105 of the expanded bag assembly 16 so that such particles when the collected blood is subsequently reinfused into the patient do not enter and cause blockage of the fine filter conventionally used in the infusion line. The filter is connected about the inlet 22 and gas outlet 30 so that both of them communicate with the interior of the filter and are in direct fluid communication with each other. Since air or gas from the inlet 22 can pass directly to outlet 30, that is, without passing through filter screen 122, the suction or negative pressure does not cause blood within the filter to mix with air and cause foaming. That is, blood is not churned by the suction force tending to produce air bubble or foam.

This configuration also provides a safeguard in that, should the filter become blocked to the point that blood can no longer pass through it, any further blood emanating from the patient will since continue to flow out through the outlet tube 30 and into the collection chamber 40 of the chest drainage unit 14, thus protecting the patient by maintaining normal suctioning.

Furthermore, should the bag 64 become over filled with blood, blood could overlfow through tube 30 and into the collection chamber 40. It is preferable to remove the autotransfusion device 12 from the chest drainage unit 14 when the blood collected in the bag 64 reaches a predetermined desired amount or, as would normally be the case, after a predetermined length of time.

When it is desired to infuse the patient with his own blood, tube clamps indicated at 154 and 156 and a patient tube clamp 160, which are open during blood collection, are actuated to close tubes 24 and 28 and 32. Then the patient tube 28 and tube 34 may be disconnected from the tube connectors 26 and 36 so as to free the autotransfusion device 12 from the chest drainage unit 14. Tubes 28 and 34 are then connected together and the patient tube clamp 160 released so that patient chest drainage suction is maintained. Next, the blood collection and reinfusion bag assemby 16 can be slid upwardly and out of holder 18 and connected to a suitable frame or the like near the patient such as by using a hanger strap that may be provided at the top of the unit (not shown). By momentarily releasing clamp 156 and gently squeezing the bag assembly 16, excess air can be eliminated from the bag. Next, cap 74 at the bottom of the bag assembly can be removed from the blood outlet 72 whereupon a conventional spike can be inserted through the piercable seal 75 closing the outlet 72, the spike being connected to an infusion tube or catheter via a filter and drip chamber to infuse the patient's blood from the bag back into the same patient.

Should it be deemed necessary to collect further blood for reinfusion to the patient, the assembly 12 may be disconnected from the chest drainage unit 14, discarded and replaced by a new bag and holder assembly 12. To connect a new assembly 12 after the previous one has been discarded, and with, the patient tube clamp 160 closed, the patient tube 28 is connected to the new tube 24 by connector 26 to connect the new bag assembly inlet 22 with patient tube 28. Tube 34 is then connected to the new bag assembly outlet tube 32 and 30. Functioning is resumed by releasing patient tube clamp 160.

The stiffener members 76 and 78 of bag assembly 16, when the assembly is in a holder 18, provide the blood collection container bag or predetermined volume similar to a container having rigid sidewalls. At the same time, since the blood collection bag assembly 16 is also collapsible, it can be used similar to a conventional collapsible blood collection bag. Also, a conventional well-known blood bag pressurizing sleeve can be used to squeeze the assembly 16 to thereby infuse blood at a rate faster than that accomplished by use of gravity only.

Because there is direct fluid communication between the inlet 22 and outlet 30, that is, communication independently of the filter 120, the suction to the patient will be maintained even if the filter 120 becomes clogged. In contrast, where a filter is placed in the patient drain line upstream of the collection container, as in prior drainage systems, should such a filter become clogged, the suction to thepatient would be reduced or cut-off and this would endanger the patient.

Preferably, the autotransfusion device 12 is assembled at the factory so that the bag assemby 16 is in the expanded condition in the holder 18 with sterile air in the bag 64. However, where desired, the bag assembly 16 could be supplied in flattened or collasped condition if a vent with an air filter is employed.

The holder 18 and chest drainage device housing may be formed of acrylic material as wll as other relatively rigid plastics. Preferably, the stiffener, holder, bag and chest drainage unit are formed of transparent plastic so that blood can be seen and monitored during operation of the system.

As various changes could be made in the above construction and without departing from the scope of the invention, it is intended that all matter contained in the above description and drawings shall be interpreted as illustrative and not in a limiting sense.

What is claimed is:

1. A body fluid collection device comprising a collapsible bag assembly including a bag having a pair of opposed sidewalls and an inlet in fluid communication with the interior of said bag for receiving body fluid, and a pair of relatively stiff flexible members respectively connected to said sidewalls, said members having portions between the opposed side edges thereof bendable outwardly in opposite directions from each other to expand said bag in response to the application of a force tending to move said opposed side edges generally toward each other, each of said members having a pair of slots adjacent each of the opposite ends thereof, each of said slots having spaced opposed sidewalls, each pair slots extending inwarding from the opposed side edges of the member adjacent each of the opposite ends thereof.

2. The device of claim 1 wherein said flexible members are respectively fixed to the outer surfaces of said sidewalls of the bag.

3. The device of claim 1 wherein the sidewalls of each of said slots converge at a point inwardly of the periphery of the member.

4. The device of claim 2 wherein the sidewalls of each of the slots are farthest apart at the periphery of the stiffener member.

5. The device of claim 4 wherein the inner ends of the slots of each pair of slots define a portion of the stiffener member of smaller width than portions of the stiffener member above and below the defined portion.

6. The device of claim 1 wherein, at each end of each of said stiffener members, each pair of slots defines a neck portion inwardly spaced from the end of the stiffener and a relatively wide portion between the neck portion and the end of stiffener member.

7. The device of claim 1 further includes a holder for maintaining a force on the opposed sides of said stiffener members to maintain the stiffener members bent outwardly and said bag expanded.

8. The device of claim 7 wherein said holder is a generally tubular member having an inner diameter less than the width of said stiffener members.

9. The device of claim 8 wherein said holder includes means for releasably connecting said holder to a chest drainage unit.

10. The device of claim 1 further includes a filter adjacent to the upper portion of said bag connected to filter blood from said inlet to the lower portion of said bag, and a gas outlet adjacent said inlet and in direct fluid communication with said inlet whereby gas can flow from said inlet without flowing through said filter.

11. The device of claim 1 wherein said inlet is connected at the upper end portion of said bag, and said bag further includes a gas outlet spaced from said inlet at the upper end portion of said bag.

12. The device of claim 1 wherein said flexible members are heat bonded to the outer surfaces of the opposed walls of said bag and substantially over the entire meeting surfaces of the walls and flexible members.

13. The device of claim 12 further including a tubular fluid outlet at the bottom of said bag whereby said bag assembly can be emptied therethrough.

14. The device of claim 1 including a cylindrical holder for maintaining opposed forces on the opposed side edges of said bag assembly to shape said bag assembly so tht it has a generally cylindrical shape in the main central portion thereof, a generally wedge shape at the top, and a generally concial shape at the bottom.

15. The device of claim 1 wherein each of said slots has a longitudinal axis at an angle of about 22° with respect to a line normal to the longitudinal axis of said bag.

16. An autotransfusion device comprising a collapsible blood collection and infusion bag having a pair of opposed pliable panels of sheet material sealed together, an inlet and a gas outlet connected at the upper end of the bag, a pair of resilient, flexible stiffener members of sheet material which is more rigid than said material of said panels connected to the outer surfaces of said panels in parallel relation with each other, each of said stiffener members having respectively at the upper and lower ends thereof a pair of slots with spaced sidewalls, the slots of each pair extending inwardly from the opposed sides of each of the stiffener member defining a tab portion at each of the upper and lower ends of each of the stiffener members connected respectively by relatively narrow flexbile necks to a central main portion of each of the stiffener members, and holder means for receiving said bag and said stiffener members sized to maintain a compressive force on said stiffener members to cause said stiffener members to be bowed outwardly from each other to cause said bag to be in expaned condition with each of said panels having different axes of symmetry for receiving blood, and means for connecting said gas outlet to a source of suction.

17. The device of claim 15 wherein said connecting means includes a chest drainage unit.

18. The device of claim 16 further including a filter connected within said bag in the upper portion thereof, said filter being connected to receive and pass blood flow from said inlet to the lower portions of said bag and said gas outlet being in direct fluid communication with said inlet in by-passing relation with said filter.

* * * * *